(12) United States Patent
Kakinuma et al.

(10) Patent No.: US 9,000,228 B2
(45) Date of Patent: Apr. 7, 2015

(54) METHOD FOR PRODUCING VINYL ETHER

(75) Inventors: Shinichi Kakinuma, Kanagawa (JP); Shinya Mita, Toyama (JP); Masahiro Murotani, Kanagawa (JP)

(73) Assignee: Nippon Carbide Industries Co., Ltd., Tokyo (JP)

( * ) Notice: Subject to any disclaimer, the term of this patent is extended or adjusted under 35 U.S.C. 154(b) by 522 days.

(21) Appl. No.: 13/375,180

(22) PCT Filed: May 28, 2010

(86) PCT No.: PCT/JP2010/059488
§ 371 (c)(1),
(2), (4) Date: Nov. 29, 2011

(87) PCT Pub. No.: WO2010/137742
PCT Pub. Date: Dec. 2, 2010

(65) Prior Publication Data
US 2012/0083628 A1 Apr. 5, 2012

(30) Foreign Application Priority Data

May 29, 2009 (JP) ................................. 2009-129969

(51) Int. Cl.
*C07C 41/08* (2006.01)
*C07C 43/18* (2006.01)
*C07D 233/70* (2006.01)

(52) U.S. Cl.
CPC .............. *C07D 233/70* (2013.01); *C07C 41/08* (2013.01); *C07C 2101/14* (2013.01)

(58) Field of Classification Search
CPC ......................... C07C 2101/14; C07C 2103/74
USPC ........................................................ 568/688
See application file for complete search history.

(56) References Cited

U.S. PATENT DOCUMENTS

2003/0114715 A1    6/2003    Boettcher et al.

FOREIGN PATENT DOCUMENTS

| GB | 616197 A | 1/1949 |
|---|---|---|
| GB | 838020 A | 6/1960 |
| JP | 35-318 B1 | 1/1960 |
| JP | 48-10013 A | 2/1973 |
| JP | 4-198144 A | 7/1992 |
| JP | 10-182536 A | 7/1998 |
| JP | 10-279513 A | 10/1998 |
| JP | 2003-73321 | 3/2003 |
| JP | 2003-286216 A | 10/2003 |
| JP | 2005-187703 A | 7/2005 |
| JP | 2008-137974 A | 6/2008 |
| JP | 2010-053087 | * 3/2010 ............ C07C 43/162 |

OTHER PUBLICATIONS

Article 94(3) EPC communication issued in European Patent Application No. 10780693.7, dated Sep. 3, 2013.
International Search Report issued in international application No. PCT/JP2010/059488.
Sims, et al., "Vapor Phase Vinylation of Aliphatic Monohydric Alcohols", Ind. Eng. Chem. Prod. Res. Dev., vol. 2, No. 4, 1963, 293-296.
Holly, "Vinylation Rates of Primary, Secondary, and Tertiary Alcohols", J. Org. Chem., vol. 24, 1959, 1752-1755.
Trofimov, "New Intermediates for Organic Synthesis based on Acetylene", Z. Chem. Bd. 26, 1986, Heft 2, 41-49.
Oparina et al., "Neucleophilic Addition to Acetylenes in Superbasic Catalytic Systems . . . ", Russian Journal of Organiz Chemistry, vol. 41, No. 5, 2005, 656-660.
Nozakura et al., "Synthesis and Polymerization of Vinyl Esters and Vinyl Ethers Having Bulky Substituents", Journal of Polymer Science, Polymer Chemistry Edition, 1973, 11(5), 1043-1051.
Boach, et al., "Synthesis of Allyl and Alkyl Vinyl Ethers Using an in Situ Prepared Air-Stable Palladium Catalyst . . . ", J. Org. Chem., vol. 68, 2003, 5225-5227.

* cited by examiner

*Primary Examiner* — Rosalynd Keys
(74) *Attorney, Agent, or Firm* — Rader, Fishman & Grauer PLLC

(57) ABSTRACT

A method for efficiently producing high purity vinyl ether represented by the following formula (1) from tertiary alcohol having a low reactivity comprising by reacting acetylene and a tertiary alcohol in the presence of a base using, as a solvent, a cyclic urea compound or glyme compound or mixture thereof:

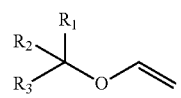

(1)

is provided.

9 Claims, 2 Drawing Sheets

METHOD FOR PRODUCING VINYL ETHER

TECHNICAL FIELD

The present invention relates to a method for producing a vinyl ether by reacting a tertiary alcohol having a low reactivity with acetylene in the presence of a base.

Vinyl ether is an industrially important compound which is used, as a monomer ingredient of a coating resin, binder, adhesive, printing ink, resist resin, etc., which can impart various characteristics to synthetic resins etc., and which is also utilized for intermediates of pharmaceuticals, agrochemicals, etc. For example, compounds produced by the present invention, such as 1-adamantylvinyl ether and 1-methylcyclohexylvinyl ether are excellent in transparency to short wavelength light and in dry etching resistance, and therefore, are promising for use for resist applications using ArF excimer lasers or other short wavelength light, as a light source or as a resist composition suitable for electron beam lithography.

BACKGROUND ART

A vinyl ether is conventionally produced by the Reppe reaction, in which an alcohol and acetylene are reacted in the presence of an alkali metal catalyst at a high temperature of 120 to 200° C. The Reppe reaction proceeds quickly and is an effective means for producing a vinyl ether when the starting alcohol is rich in reactivity such as a primary or secondary alcohol. However, there is the problem that, for an alcohol having a low reactivity such as a tertiary alcohol, the alcohol conversion is not sufficient and, further, the vinylization does not proceed completely (Non-Patent Literatures 1 and 2).

Further, the method for reacting the alcohol and acetylene in a so-called super basic medium has been reported. For example, the method for using an alkali metal hydroxide, as a catalyst, and performing the reaction in an aprotic polar solvent to efficiently produce a vinyl ether has been reported (Non-Patent Literature 3). However, while this method is fast in reaction and excellent in alcohol conversion rate and vinyl ether production rate in the case of a primary and secondary alcohols, it has the problem of a low yield in the case of vinylization of a tertiary alcohol.

Furthermore, an improved method for reacting an alcohol with acetylene in a super basic medium has also been reported. That is, the method for accelerating the reaction by forming anhydrous cesium hydroxide in the reaction system and using it as a catalyst has been reported (Non-Patent Literature 4). However, in this method as well, when performing the reaction under an acetylene initial pressure of 16 atm, the conversion rate of the tertiary alcohol, i.e., t-butanol is 25%, while the yield of the vinyl ether is 8%, i.e., insufficient. Further, when performing the reaction under an acetylene pressure of atmospheric pressure, it is also described that not even a trace amount of t-butylvinyl ether can be detected.

In addition, it is reported that, after a catalyst is prepared by reacting a tertiary alcohol, i.e., 1-adamantanol and tri(n-propyl)carbinol with metal potassium in a toluene solvent the vinylization is carried out under a 18 kg/cm² acetylene initial pressure (Non-Patent Literature 5). However, in this method as well, despite the reaction being carried out under a high acetylene pressure, the yield is a low as 67 to 40%, and therefore the method is not said to be sufficient.

Furthermore, the method for obtaining the desired vinyl ether by using a relatively easily obtainable alkylvinyl ether from an ether exchange reaction of alcohol in the presence of a metal catalyst is known in the art. For example, the method for reacting n-butylvinyl ether and the tertiary alcohol, i.e., t-butanol and 1-adamantanol in the presence of a palladium catalyst stable in the air is reported (Non-Patent Literature 6). However, there are the problems with this method that the yield is a low as 72 to 61%, a long time of 32 to 48 hours is required for equalization, an amount of alkylvinyl ether used is 20 times of the alcohol and thus the productivity is of low.

As explained above, in the conventional method for producing vinyl ether, when the vinylization of alcohol is insufficient, separation by distillation is not efficient, because vinyl ether and alcohol have similar structures. For this reason, production of high purity vinyl ether causes a high load on the purification process and features a low yield, and therefore the problem is a high production cost.

As a solution, an efficient vinylization method of alcohol having a low reactivity is proposed. Patent Literature 1 discloses a method for reacting an alcohol with acetylenes in a liquid phase in the presence of a co-catalyst such as a basic alkali metal compound and 1,4-diethoxybutane or 1,4-divinyloxybutane. However, to achieve a sufficient conversion of the alcohol by this method in a short time, as disclosed in the examples, a high acetylene pressure of about 20 kg/cm² (absolute pressure) is required. Acetylene is extremely unstable under a pressure exceeding 2 kg/cm² (gauge pressure) and a self decomposition and explosion easily occurs. The higher the pressure, the higher the risk. The above method is not preferable in terms of safety. Further, Patent Literature 1 describes use of phenol as a starting material and synthesis of phenylvinyl ether in an N-methyl-2-pyrrolidone solvent, but does not describe in any way the use of a tertiary solid alcohol as a starting material.

As another method, the method for reacting a vinyl ester compound and alcohol in the presence of a metal catalyst to obtain the corresponding vinyl ether is known. For example, the method for using an iridium compound, as a transition metal catalyst, and for reacting vinyl acetate and 1-adamantanol in a toluene solvent in the presence of sodium carbonate by an ester exchange reaction to obtain a desired product is disclosed (Patent Literature 2). In this method, the conversion rate of 1-adamantanol reaches 93% and the yield of the desired product is also as high as 91%. However, in addition to unconverted alcohol, about 1% of unnecessary by-product is formed. This method is not said to be sufficient for obtaining a high purity product. Furthermore, an expensive iridium catalyst is used, the reaction system is dilute, the productivity is low, and other issues remain to be solved.

PRIOR ART LIST

Non-Patent Literature

Non-Patent Literature 1: Ind. Eng. Chem. Prod. Res. Dev., Vol. 2, No. 4, 1963, 293-296.

Non-Patent Literature 2: J. Org. Chem., Vol. 24, 1959, 1752-1755

Non-Patent Literature 3: Z. Chem. Bd. 26, 1986, Heft 2, 41-49.

Non-Patent Literature 4: Russian Journal of Organic Chemistry, Vol. 41, No. 5, 2005, 656-660.

Non-Patent Literature 5: Journal of Polymer Science, Polymer Chemistry Edition, 1973, 11(5), 1043-1051.

Non-Patent Literature 6: J. Org. Chem., Vol. 68, 2003, 5225-5227.

Patent Literature

Patent Literature 1: Japanese Patent Publication No. 2003-530375A
Patent Literature 2: Japanese Patent Publication No. 2003-73321A

SUMMARY OF INVENTION

Technical Problem to be Solved

As explained above, in a method of synthesis of vinyl ether reported up to now, it is not possible to vinylize the tertiary alcohol at a low acetylene pressure by a high conversion rate. Therefore, a method for vinylizing a tertiary alcohol having a low reactivity safely and industrially to produce vinyl ether is being sought. Note that the 1-methylcyclohexylvinyl ether according to the present invention has never been reported in the past and is considered a novel compound.

Means for Solving Problem

The inventors engaged in an in-depth study for solving the problem and, as a result, found a method for reacting acetylene and a tertiary alcohol in the presence of a base by using a cyclic urea compound or glyme compound or mixtures thereof, as a solvent, to safely and industrially vinylize a tertiary alcohol, whereby the present invention has been completed.

That is, the present invention provides a method for producing vinyl ether represented by the following formula (1):

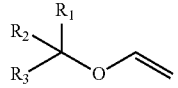
(1)

from acetylene and a tertiary alcohol in the presence of a base, characterized in that the tertiary alcohol is an alcohol represented by the following formula (2):

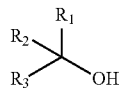
(2)

and that the reaction is carried out by using, as a solvent, a cyclic urea compound represented by the following formula (3) or a glyme compound represented by the following formula (4), or the mixture thereof.

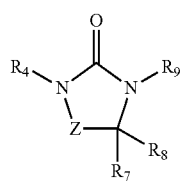
(3)

wherein Z indicates

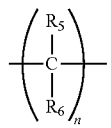

$R_{10}O(CH_2CH_2O)_lR_{11}$ (4)

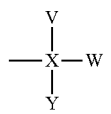
(5)

In the formulae (1) to (4),
$R_1$ to $R_3$ independently indicate the $C_1$ or more hydrocarbon groups represented by the above formula (5),
wherein
X is a carbon atom,
V and W independently indicate hydrogen or a substituted or unsubstituted $C_1$ or more hydrocarbon group, provided that the case where the carbon directly bonded with X of V or W has a primary or secondary hydroxyl group in a cis arrangement with a hydroxyl group of the tertiary alcohol (2), as a substituent group is excluded, and Y indicates hydrogen or a substituted or unsubstituted $C_1$ or more hydrocarbon group, provided that the case where the carbon of Y directly bonded with X has a primary or secondary hydroxyl group in a cis arrangement with a hydroxyl group of the tertiary alcohol (2), as a substituent group is excluded; or one group selected from a tertiary hydroxyl group, alkoxy group and alkyl sulfanyl group,
two or more of $R_1$ to $R_3$ may be condensed to form a ring, provided that the case where two or more of $R_1$ to $R_3$ are condensed to form an aromatic ring is excluded,
further, $R_4$ to $R_9$ independently indicate hydrogen or a $C_1$ or more alkyl group or —$(CH_2CH_2O)_mR_{10}$, $R_{10}$ and $R_{11}$ independently indicate hydrogen or a $C_1$ to $C_4$ saturated or unsaturated hydrocarbon group,
l and m are independently integers of 1 or more, and
n is an integer of 1 to 4.

Advantageous Effects of Invention

According to the present invention, it is possible to vinylize a tertiary alcohol having a low reactivity under a low acetylene pressure with a short time and efficiently to produce a high purity vinyl ether.

EMBODIMENTS FOR CARRYING OUT THE INVENTION

Figure 1:
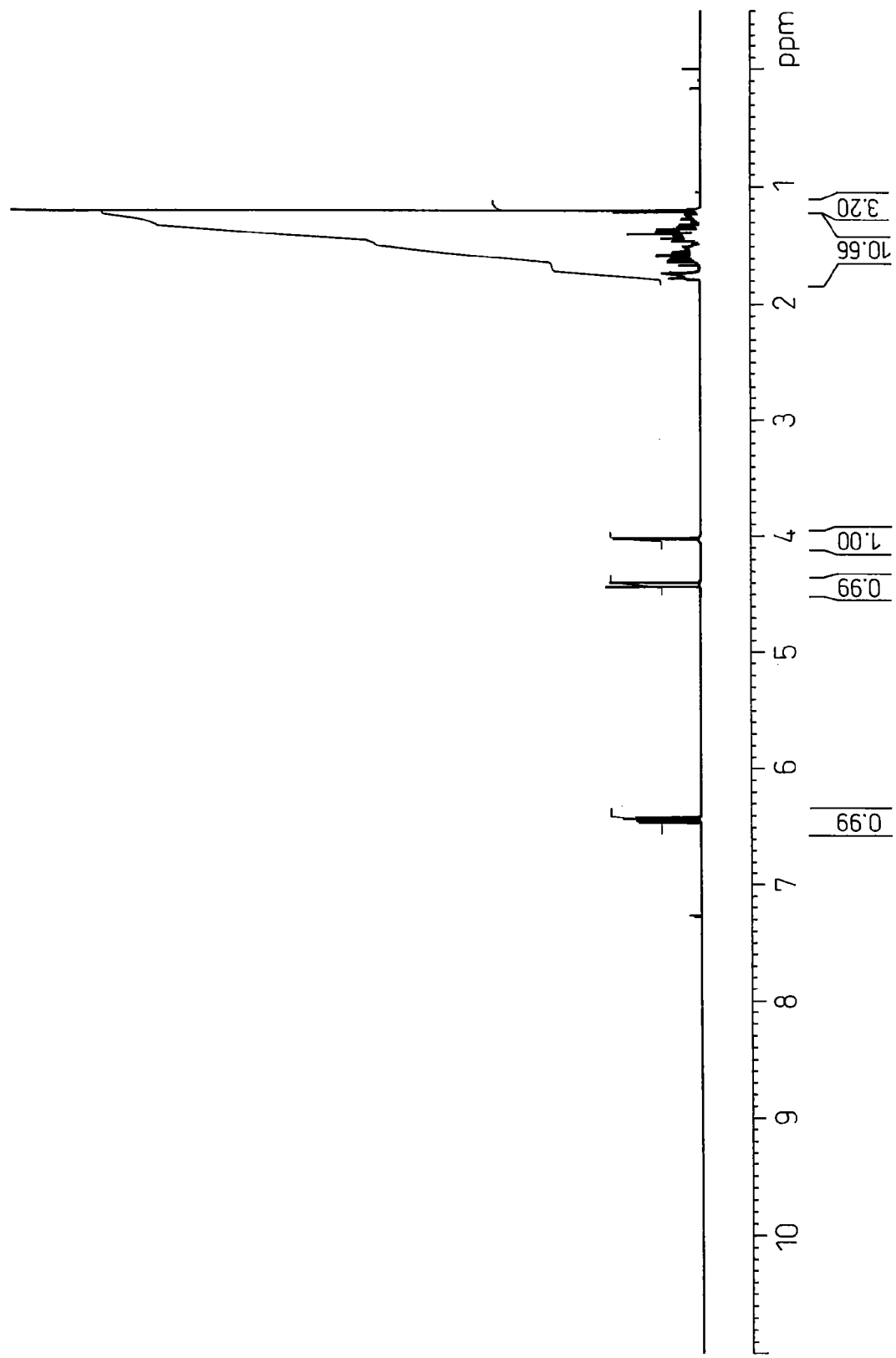
FIG. 1 is an $^1$H-NMR chart of 1-methylcyclohexylvinyl ether synthesized in Example 11.
Figure 2:
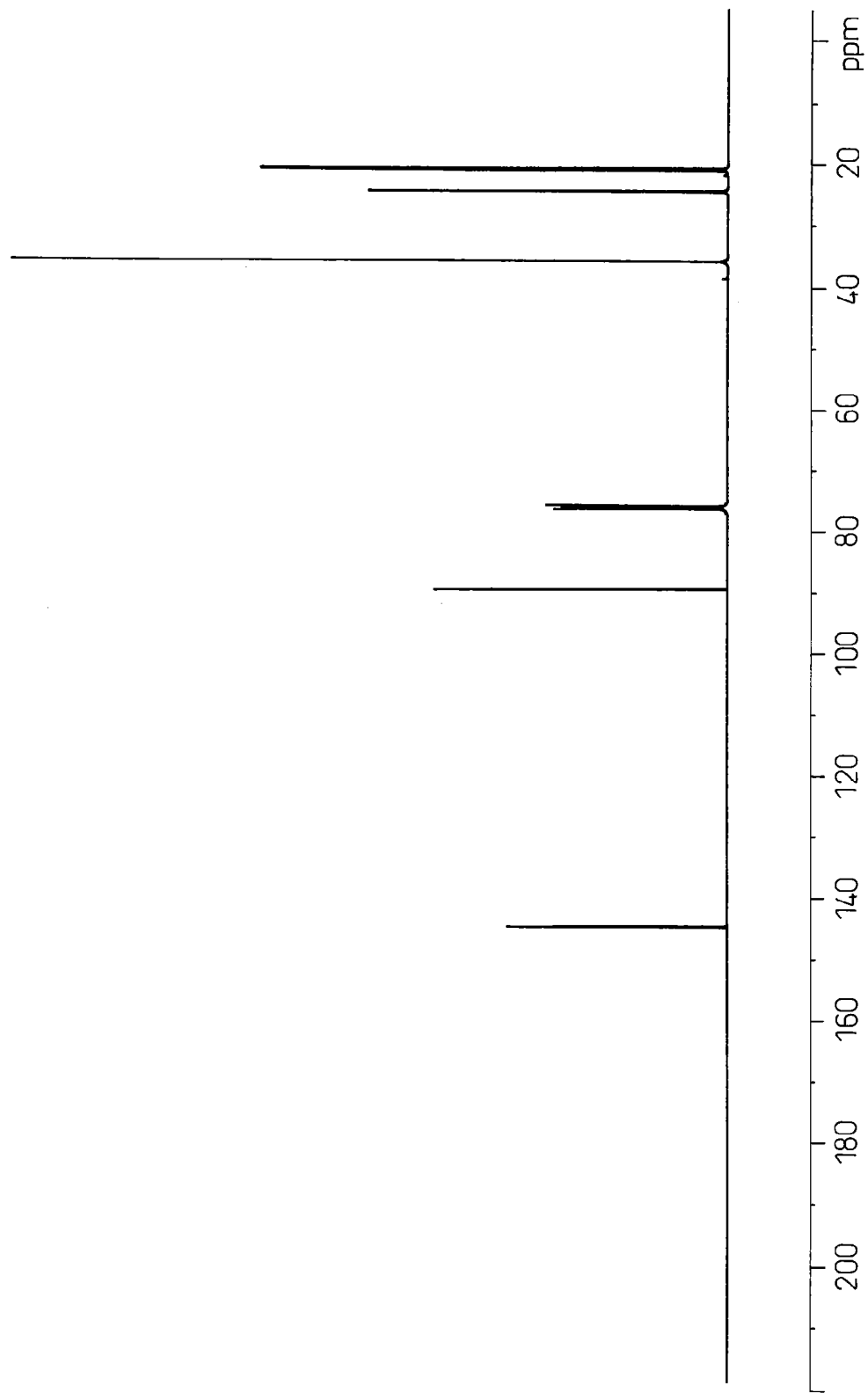
FIG. 2 is a $^{13}$C-NMR chart of 1-methylcyclohexylvinyl ether synthesized in Example 11.

The present invention will now be described in detail.

The present invention provides a method for producing a vinyl ether represented by the following formula (1) from acetylene and a tertiary alcohol in the presence of a base

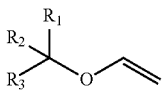
(1)

and
the tertiary alcohol is an alcohol represented by the following formula (2):

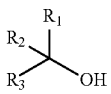
(2)

and a reaction is carried out by using, as a solvent, a cyclic urea compound represented by the following formula (3), a glyme compound represented by the following formula (4), or the mixture thereof.

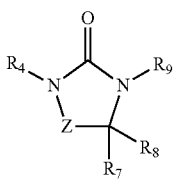
(3)

wherein Z indicates:

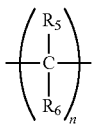

$R_{10}O(CH_2CH_2O)_lR_{11}$ (4)

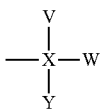
(5)

In formulae (1) to (4),
$R_1$ to $R_3$ independently indicate the $C_1$ or more hydrocarbon groups represented by formula (5),
wherein
X is a carbon atom,
V and W independently indicate hydrogen or a substituted or unsubstituted $C_1$ or more hydrocarbon group, provided that the case where the carbon directly bonded with X of V or W has a primary or secondary hydroxyl group in a cis arrangement with a hydroxyl group of the tertiary alcohol (2), as a substituent group is excluded, and Y indicates hydrogen or a substituted or unsubstituted $C_1$ or more hydrocarbon group, provided that the case where the carbon of Y directly bonded with X has a primary or secondary hydroxyl group in a cis arrangement with a hydroxyl group of the tertiary alcohol (2), as a substituent group is excluded; or one group selected from a tertiary hydroxyl group, alkoxy group and alkyl sulfanyl group, two or more of $R_1$ to $R_3$ may be condensed to form a ring, provided that the case where two or more of $R_1$ to $R_3$ are condensed to form an aromatic ring is excluded,
further, $R_4$ to $R_9$ independently indicate hydrogen or a $C_1$ or more alkyl group or —$(CH_2CH_2O)_mR_{10}$, $R_{10}$ and $R_{11}$ independently indicate hydrogen or a $C_1$ to $C_4$ saturated or unsaturated hydrocarbon group,
l and m are independently integers of 1 or more, and
n is an integer of 1 to 4.

The tertiary alcohol usable in the present invention is preferably one which preferentially doesn't forms an acetal ring in the molecule under the reaction conditions. When the tertiary alcohol usable in the present invention has two or more hydroxyl groups in the molecule, if the reaction proceeds and one of two or more hydroxy groups is vinylized, sometimes this vinyl group and another hydroxyl group will form a ring in the molecule to thereby form an acetal ring. If this side reaction ring-forming reaction in the molecule proceeds with priority, sometimes the desired product cannot be obtained, and therefore this is not preferred. Therefore, in the tertiary alcohol represented by the formula (2) used in the present invention,
$R_1$ to $R_3$ independently indicate $C_1$ or more hydrocarbon groups represented by the above formula (5),
wherein
X indicates a carbon atom,
V and W independently indicate hydrogen or a substituted or unsubstituted $C_1$ or more hydrocarbon group, provided that the case where the carbon directly bonded with X of V or W has a primary or secondary hydroxyl group in a cis arrangement with a hydroxyl group of the tertiary alcohol (2), as a substituent group is excluded, and Y indicates hydrogen or a substituted or unsubstituted $C_1$ or more hydrocarbon group, provided that the case where the carbon of Y which directly bonds with X has a primary or secondary hydroxy group in a cis arrangement with the hydroxyl group of the tertiary alcohol (2), as a substituent group is excluded; or one group selected from a tertiary hydroxyl group, alkoxy group and alkylsulfanyl group, two or more of $R_1$ to $R_3$ may be condensed to form a ring, provided that the case where two or more of $R_1$ to $R_3$ are condensed to form an aromatic ring is excluded.

The above-mentioned substituent groups in the formulae of the present invention may be any structure which is inert in the reaction system and does not hinder the reaction. For example, an alkoxy group, alkylsulfanyl group, hydroxyl group, etc. may be mentioned. As preferable examples of $R_1$, $R_2$, and $R_3$, a substituted or unsubstituted alkyl group and cycloalkyl group may be mentioned. In particular, an unsubstituted alkyl group or cycloalkyl group is preferable.

As specific examples of the alcohol in the present invention, t-butanol, 2-methyl-2-butanol, 2-methyl-2-pentanol, 2-methyl-2-hexanol, 3-ethyl-3-pentanol, 9-octyl-9-heptadecanol, 2,3-dimethyl-2-butanol, 2,5-dimethyl-2,5-hexanediol, 2,6-dimethyl-2-heptanol, 3-methyl-1,3-butanediol, 3,3,4-trimethyl-1,4-pentanediol, 1-methylcyclohexanol, 1,1,1-tricyclohexylmethanol, 1-adamantanol, adamantane-1,3-diol, 2-methyl-2-adamantanol, 2-(1-adamantyl)propan-2-ol, terpinene-4-ol, α-terpineol, 2-methyl-3-buten-2-ol, linalool, geranyllinalool, isophytol, dihydromyrcenol, 25-hydroxyvitamin D2, 2-methyl-1-phenyl-2-propanol, 2-phenyl-2-propanol, 2-phenylpentan-2-ol, 1,1-diphenylethanol, 1,1,1-triphenylmethanol, 1-cyclopropyl-1,1-diphenylmethanol, 1-phenyl-1-cyclohexanol, 1,1-dicyclopropyl-1-phenylmethanol, bis-(4-hydroxy-1-naphthyl)phenylmethanol, 9-phenyl-9-fluorenol, etc. may be mentioned, but the invention is not limited to these.

The base in the production method of the present invention is not particularly limited, but an alkali metal compound can be used. As the alkali metal compound, for example, sodium hydroxide, potassium hydroxide, rubidium hydroxide, cesium hydroxide, alcoholates obtained by reaction of these hydroxides and alcohol, etc. may be mentioned. As particularly preferable bases, potassium hydroxide and potassium t-butoxy may be mentioned. The amount of use of the base is not particularly limited, but usually the amount is about 1 to 200 mol %, based upon the alcohol. The use of 5 to 100 mol % is preferable, and the use of 10 to 60 mol % is more preferable.

The pressure of the acetylene in the production method of the present invention is not particularly limited, but from the viewpoint of safety, it is preferably 2 kg/cm² (gauge pressure) or less, more preferably atmospheric pressure to 1.8 kg/cm² (gauge pressure).

The reaction temperature in the production method of the present invention is not particularly limited, but is preferably 120 to 180° C., more preferably 140 to 160° C.

As the reaction solvent in the production method of the present invention, a cyclic urea compound represented by the following formula (3) or a glyme compound represented by the following formula (4) or the mixture thereof is used.

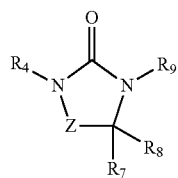

(3)

wherein Z indicates

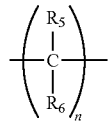

$R_{10}O(CH_2CH_2O)_l R_{11}$ (4)

In the above formulae (3) and (4), $R_4$ to $R_9$ independently indicate hydrogen or a $C_1$ or more alkyl group or $-(CH_2CH_2O)_m R_{10}$, $R_{10}$ and $R_{11}$ independently indicate hydrogen or a $C_1$ to $C_4$ saturated or unsaturated hydrocarbon group, l and m are integers of 1 or more and n is an integer of 1 to 4.

In the above formula (3), as preferable examples of $R_4$ and $R_9$, linear or branched alkyl groups and groups having alkyl or alkenyl ends and having oxyethyl units as recurring units may be mentioned. A particularly preferable example is a methyl group. Further, as preferable examples of $R_5$ to $R_8$, hydrogen and linear or branched alkyl groups may be mentioned. A particularly preferable example is hydrogen.

In the formula (4), as preferable examples of $R_{10}$ and $R_{11}$, saturated or unsaturated hydrocarbon groups and hydrogen may be mentioned. Particularly preferable examples are a methyl group and ethenyl group and l is an integer of 2 to 70.

As the reaction solvent in the production method of the present invention, it is possible to use at least one compound selected from the cyclic urea compound represented by the above formula (3) and the glyme compound represented by the above formula (4). Further, it is possible to jointly use another aprotic polar solvent or aprotic nonpolar solvent. As the reaction solvent in the present invention, from the viewpoint of the efficient progress in the reaction, it is preferable that the content of the cyclic urea compound represented by the above formula (3) or the glyme compound represented by the above formula (4) is high. More preferably, a solvent only containing of one or more compounds selected from the cyclic urea compounds represented by the above formula (3) and the glyme compound represented in the above formula (4) is used.

As representative cyclic urea compounds in the production method of the present invention, 1,3-dimethyl-2-imidazolidinone, 1,3,4-trimethyl-2-imidazolidinone, 1,3-diethyl-2-imidazolidinone, 1,3-diisopropyl-2-imidazolidinone, 1,3-dimethyltetrahydropyrimidi-2-one, etc. may be mentioned, but the invention is not limited to these. As the cyclic urea compound in the present invention, it is preferable to use 1,3-dimethyl-2-imidazolidinone or 1,3-dimethyltetrahydropyrimidi-2-one.

As representative glyme compounds in the production method of the present invention, diethylene glycol dimethyl ether, triethylene glycol dimethyl ether, tetraethylene glycol dimethyl ether, diethylene glycol divinyl ether, triethylene glycol divinyl ether, tetraethylene glycol divinyl ether, diethylene glycol, triethylene glycol, tetraethylene glycol, diethylene glycol monovinyl ether, triethylene glycol monovinyl ether, tetraethylene glycol monovinyl ether, etc. may be mentioned, but the invention is not limited to these compounds.

In the production method of the present invention, it is preferable to carried out the reaction in the presence of the above specific solvent, while maintaining the total amount of the alcohol and the resultant vinyl ether at a concentration of 17% by weight or more based upon the total amount including the other ingredients, while maintaining it at a range of concentration of 25 to 90% by weight. When a solid alcohol is used as the starting material, it is also possible to carry out the reaction in a slurry state, but the speed of absorption of the acetylene is decreased and the productivity deteriorates, and therefore, the state where the staring alcohol is dissolved in a solvent at the reaction temperature is preferred.

In the production method of vinyl ether represented by the following formula (1) of the present invention, if the total amount of the alcohol and the resultant vinyl ether is a concentration of less than 17% by weight, based upon the total amount including the other ingredients, sometimes the acetylene will not be effectively consumed for conversion of alcohol, and therefore, this is not efficient. Accordingly, in the method of production of vinyl ether represented by the following formula (1) of the present invention, it is preferable to carry out the reaction under conditions where the total of the starting alcohol and resultant vinyl ether becomes a concentration of 17% by weight or more in the reaction system. In particular, in the production method of vinyl ether represented by the following formula (1) of the present invention, it is preferable to react the total of the starting tertiary alcohol (2) and resultant vinyl ether becomes a concentration of 25 to 90% by weight in the reaction system.

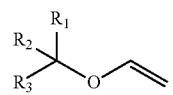

(1)

-continued

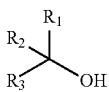
(2)

In the formulae (1) and (2), $R_1$ to $R_3$ independently indicate $C_1$ or more hydrocarbon groups represented by the following formula (5)

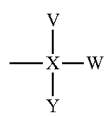
(5)

wherein

X indicates a carbon atom,

V and W independently indicate hydrogen or a substituted or unsubstituted $C_1$ or more hydrocarbon group, provided that the case where the carbon directly bonds with X of V or W has a primary or secondary hydroxyl group in a cis arrangement with a hydroxyl group of the tertiary alcohol (2) as a substituent group is excluded, and Y independently indicates hydrogen or a substituted or unsubstituted $C_1$ or more hydrocarbon group, provided that the case where the carbon of Y which directly bonds with X has a primary or secondary hydroxy group in a cis arrangement with the hydroxyl group of the tertiary alcohol (2) as a substituent group is excluded; or one group selected from a tertiary hydroxyl group, alkoxy group and alkylsulfanyl group, two or more of $R_1$ to $R_3$ may be condensed to form a ring, provided that the case where two or more of $R_1$ to $R_3$ are condensed to form an aromatic ring is excluded.

The production method of the present invention can be carried out also by any of a continuous process, semicontinuous process or batch process type of reaction. In a continuous process, it is possible to continuously supply the alcohol, basic compound, solvent and acetylene and continuously discharge the reaction mixture. In a semicontinuous process, it is possible to continuously supply a part of the alcohol, basic compound, solvent and acetylene and continuously discharge the reaction mixture. In a batch process, it is possible to charge, in advance, a part of the alcohol, basic compound, solvent and acetylene to a reactor and discharge the reaction mixture after the end of the reaction.

EXAMPLES

Examples will now be used to explain the present invention in further detail, but the present invention is not limited to these Examples of course.

Example 1

A 2000 ml volume SUS autoclave equipped with a stirrer, pressure gauge, thermometer, gas introduction pipe and gas purge line was charged with 1,3-dimethyl-2-imidazolidinone 266.8 g, 1-adamantanol 159.9 g (1.05 mol) and 95 wt % purity potassium hydroxide 6.40 g (0.11 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm². Next, while holding the gauge pressure at 1.8 kg/cm², the temperature was gradually increased. The reaction was carried out for about 1.9 hours after the reaction vessel internal temperature exceeded 121° C. During this time, the reaction was controlled so that the reaction vessel internal temperature did not exceed 160° C., then successively acetylene gas was refilled and the pressure inside the reaction vessel was held constantly at 1.8 kg/cm². After the end of the reaction, the residual acetylene gas was purged, the reaction solution was sampled, and gas chromatography was performed. As a result, the conversion of 1-adamantanol was 97.9%, while the selectivity of 1-adamantylvinyl ether was 97.3%. The volume of the absorbed acetylene (including amount dissolved in reaction solution) was 28.0 liters. This was 120% based upon the stoichiometric amount, and therefore the percent of the acetylene which was effectively utilized for vinylization was 81%.

Example 2

A 2000 ml volume SUS autoclave equipped with a stirrer, pressure gauge, thermometer, gas introduction pipe and gas purge line was charged with 1,3-dimethyl-2-imidazolidinone 266.4 g, 1-adamantanol 159.7 g (1.05 mol) and 98 wt % purity potassium t-butoxy 12.4 g (0.11 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm². Next, while holding the gauge pressure at 1.8 kg/cm², the temperature was gradually increased. The reaction was carried out for about 4.5 hours after the reaction vessel internal temperature exceeded 133° C. During this time, the reaction was controlled so that the reaction vessel internal temperature did not exceed 145° C., then successively acetylene gas was refilled and the pressure inside the reaction vessel was held constantly at 1.8 kg/cm². After the end of the reaction, the residual acetylene gas was purged, the reaction solution was sampled, and gas chromatography was performed. As a result, the conversion of 1-adamantanol was 98.1%, while the selectivity of 1-adamantylvinyl ether was 96.8%. The volume of the absorbed acetylene (including amount dissolved in reaction solution) was 28.7 liters. This was 123% based upon the stoichiometric amount, and therefore, the percent of the acetylene which was effectively utilized for vinylization was 79%.

Example 3

A 2000 ml volume SUS autoclave equipped with a stirrer, pressure gauge, thermometer, gas introduction pipe and gas purge line was charged with 1,3-dimethyl-2-imidazolidinone 266.4 g, 1-adamantanol 160.3 g (1.05 mol) and 98 wt % purity potassium t-butoxide 12.4 g (0.11 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm². Next, while holding the gauge pressure at 1.8 kg/cm², the temperature was gradually increased. The reaction was carried out for about 1.8 hours after the reaction vessel internal temperature exceeded 158° C. During this time, the reaction was controlled so that the reaction vessel internal temperature did not exceed 175° C., then successively acetylene gas was refilled and the pressure inside the reaction vessel was held constantly at 1.8 kg/cm². After the end of the reaction, the residual acetylene gas was purged to obtain the reaction solution 482.5 g. As a result of gas chromatography, the conversion of 1-adamantanol was 99.9%, while the selectivity of 1-adamantylvinyl ether was 97.1%. The volume of the absorbed acetylene (including amount dissolved in reaction solution) was 31.4 liters. This was 135% based upon the stoichiometric amount, and therefore the percent of the acetylene which was effectively utilized for vinylization was 72%.

Example 4

A 2000 ml volume SUS autoclave equipped with a stirrer, pressure gauge, thermometer, gas introduction pipe and gas purge line was charged with 1,3-dimethyl-2-imidazolidinone 478.0 g, 1-adamantanol 288.4 g (1.88 mol) and 98 wt % purity potassium t-butoxide 22.4 g (0.20 mol), nitrogen gas was run while stirring for about 60 minutes, and the inside of the vessel was replaced with nitrogen. Next, the reaction vessel was sealed and the inside of the vessel was charged with acetylene gas at a pressure of 1.8 kg/cm$^2$. Next, while holding the gauge pressure at 1.8 kg/cm$^2$, the temperature was gradually increased. The reaction was carried out for about 8.5 hours after the reaction vessel internal temperature exceeded 155° C. During this time, the reaction was controlled so that the reaction vessel internal temperature did not exceed 165° C., then successively acetylene gas was refilled and the pressure inside the reaction vessel was held constantly at 1.8 kg/cm$^2$. After the end of the reaction, the residual acetylene gas was purged to obtain the reaction solution 874.9 g. As a result of gas chromatography, the conversion of 1-adamantanol was 99.8%, while the selectivity of 1-adamantylvinyl ether was 98.3%. The volume of the absorbed acetylene (including amount dissolved in reaction solution) was 70.5 liters. This was 168% based upon the stoichiometric amount, and therefore the percent of the acetylene which was effectively utilized for vinylization was 59%.

The reaction solutions which were obtained at Examples 3 and 4 were combined. The mixture was purified by the ordinary process of distillation in vacuum, reprecipitation and recrystallization to obtain 451.4 g of dried crystal. As a result of analysis by NMR, this was high purity 1-adamantylvinyl ether (purity by gas chromatography 99.7%, yield 86.7%).

The results of NMR measurement of the 1-adamantylvinyl ether obtained above are shown.

$^1$H-NMR (CDCl$_3$, TMS, 400 MHz): δ ppm 1.59-1.83 (m, 12H), 2.18 (brs, 3H), 4.02 (dd, 1H, J=6.2, 0.7 Hz), 4.42 (dd, 1H, J=13.7, 0.7 Hz), 6.59 (dd, 1H, J=13.7, 6.2 Hz)

$^{13}$C-NMR (CDCl$_3$, 100 MHz): δ ppm 30.6, 36.2, 41.8, 75.3, 90.3, 145.0

Example 5

A 2000 ml volume SUS autoclave equipped with a stirrer, pressure gauge, thermometer, gas introduction pipe and gas purge line was charged with 1,3-dimethyl-2-imidazolidinone 345.1 g, 1-adamantanol 75.0 g (0.49 mol) and 95 wt % purity potassium hydroxide 2.89 g (0.05 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm$^2$. Next, while holding the gauge pressure at 1.8 kg/cm$^2$, the temperature was gradually increased. The reaction was carried out for about 3.7 hours after the reaction vessel internal temperature exceeded 137° C. During this time, the reaction was controlled so that the reaction vessel internal temperature did not exceed 146° C., then successively acetylene gas was refilled and the pressure inside the reaction vessel was held constantly at 1.8 kg/cm$^2$. After the end of the reaction, the residual acetylene gas was purged, the reaction solution was sampled, and gas chromatography was performed. As a result, the conversion of 1-adamantanol was 56.8%, while the selectivity of 1-adamantylvinyl ether was 55.9%. The volume of the absorbed acetylene (including amount dissolved in reaction solution) was 13.0 liters. This was 119% based upon the stoichiometric amount, and therefore, the percent of the acetylene which was effectively utilized for vinylization was 47%.

Example 6

A 2000 ml volume SUS autoclave equipped with a stirrer, pressure gauge, thermometer, gas introduction pipe and gas purge line was charged with 1,3-dimethyl-2-imidazolidinone 376.7 g, 1-adamantanol 250.5 g (1.65 mol) and 95 wt % purity potassium hydroxide 11.1 g (0.19 mol), nitrogen gas was run, while stirring for about 60 minutes, and the inside of the vessel was replaced with nitrogen. Next, while raising the temperature, the atmosphere inside of the reaction vessel was changed from nitrogen gas to acetylene gas. After the vessel internal temperature reached 147° C., acetylene gas was run at a flow rate of 0.3 ml/min under atmospheric pressure. Starting from this point, the reaction was carried out for about 62 hours. Further, during this time, to prevent a drop in the reaction speed, potassium hydroxide 11.8 g (0.20 mol) was added in the middle and the reaction was controlled so that the reaction vessel internal temperature did not exceed 160° C. After the end of the reaction, the residual acetylene gas was purged, then the reaction solution 686.2 g was obtained. As a result of the gas chromatography, the conversion of 1-adamantanol was 97.2%, while the selectivity of 1-adamantylvinyl ether was 97.1%. In Example 6, the total amount of the acetylene run was 1107 L, but, if desired, it is possible to use the method for circulating the unreacted acetylene again to the reaction tank to effectively reutilize the acetylene and suppress the net amount of consumption.

Example 7

A 2000 ml volume SUS autoclave equipped with a stirrer, pressure gauge, thermometer, gas introduction pipe and gas purge line was charged with 1,3-dimethyltetrahydropyrimidi-2-one 265.3 g, 1-adamantanol 161.1 g (1.06 mol) and 95 wt % purity potassium hydroxide 6.37 g (0.11 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm$^2$. Next, while holding the gauge pressure at 1.8 kg/cm$^2$, the temperature was gradually increased. The reaction was carried out for about 6.8 hours after the reaction vessel internal temperature exceeded 132° C. During this time, the reaction was controlled so that the reaction vessel internal temperature did not exceed 146° C., then successively acetylene gas was refilled and the pressure inside the reaction vessel was held constantly at 1.8 kg/cm$^2$. After stopping the reaction, the residual acetylene gas was purged, the reaction solution was sampled, and gas chromatography was performed. As a result, the conversion of 1-adamantanol was 50.0%, while the selectivity of 1-adamantylvinyl ether was 49.7%. The volume of the absorbed acetylene (including amount dissolved in reaction solution) was 17.7 liters. This was 75% based upon the stoichiometric amount, and therefore, the percent of the acetylene which was effectively utilized for vinylization was 66%.

Example 8

A 2000 ml volume SUS autoclave equipped with a stirrer, pressure gauge, thermometer, gas introduction pipe and gas purge line was charged with triethylene glycol dimethyl ether 266.8 g, 1-adamantanol 155.8 g (1.02 mol) and 95 wt % purity potassium hydroxide 6.39 g (0.11 mol), nitrogen gas was run while stirring for about 60 minutes, and the inside of the vessel was replaced with nitrogen. Next, the reaction vessel was sealed and the inside of the vessel was charged with acetylene gas at a pressure of 1.8 kg/cm². Next, while holding the gauge pressure at 1.8 kg/cm², the temperature was gradually increased. The reaction was carried out for about 19.2 hours after the reaction vessel internal temperature exceeded 137° C. During this time, the reaction was controlled so that the reaction vessel internal temperature did not exceed 170° C., then successively acetylene gas was refilled and the pressure inside the reaction vessel was held constantly at 1.8 kg/cm². After the end of the reaction, the residual acetylene gas was purged, the reaction solution was sampled, and gas chromatography was performed. As a result, the conversion of 1-adamantanol was 77.5%, while the selectivity of 1-adamantylvinyl ether was 77.1%. The volume of the absorbed acetylene (including amount dissolved in reaction solution) was 23.3 liters. This was 103% based upon the stoichiometric amount, and therefore, the percent of the acetylene which was effectively utilized for vinylization was 75%.

Example 9

A 2000 ml volume SUS autoclave equipped with a stirrer, pressure gauge, thermometer, gas introduction pipe and gas purge line was charged with tetraethylene glycol dimethyl ether 265.5 g, 1-adamantanol 160.1 g (1.05 mol) and 95 wt % purity potassium hydroxide 6.39 g (0.11 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm². Next, while holding the gauge pressure at 1.8 kg/cm², the temperature was gradually increased. The reaction was carried out for about 13.3 hours after the reaction vessel internal temperature exceeded 137° C. During this time, the reaction was controlled so that the reaction vessel internal temperature did not exceed 146° C., then successively acetylene gas was refilled and the pressure inside the reaction vessel was held constantly at 1.8 kg/cm². After stopping the reaction, the residual acetylene gas was purged, the reaction solution was sampled, and gas chromatography was performed. As a result, the conversion of 1-adamantanol was 37.4%, while the selectivity of 1-adamantylvinyl ether was 36.8%. The volume of the absorbed acetylene (including amount dissolved in reaction solution) was 13.3 liters. This was 57% based upon the stoichiometric amount, and therefore, the percent of the acetylene which was effectively utilized for vinylization was 65%.

Example 10

A 2000 ml volume SUS autoclave equipped with a stirrer, pressure gauge, thermometer, gas introduction pipe and gas purge line was charged with 1,3-dimethyl-2-imidazolidinone 395.8 g, 1-adamantanol 25.1 g (0.16 mol) and 95 wt % purity potassium hydroxide 0.98 g (0.02 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm². Next, while holding the gauge pressure at 1.8 kg/cm², the temperature was gradually increased. The reaction was performed for about 4.3 hours after the reaction vessel internal temperature exceeded 137° C. During this time, the reaction was controlled so that the reaction vessel internal temperature did not exceed 147° C., then successively acetylene gas was refilled and the pressure inside the reaction vessel was held constantly at 1.8 kg/cm². After the end of the reaction, the residual acetylene gas was purged, the reaction solution was sampled, and gas chromatography was performed. As a result, the conversion of 1-adamantanol was 27.8%, while the selectivity of 1-adamantylvinyl ether was 27.1%. The volume of the absorbed acetylene (including amount dissolved in reaction solution) was 3.6 liters. This was 98% based upon the stoichiometric amount, and therefore the percent of the acetylene which was effectively utilized for vinylization was 28%.

Example 11

A 2000 ml volume SUS autoclave equipped with a stirrer, pressure gauge, thermometer, gas introduction pipe and gas purge line was charged with 1,3-dimethyl-2-imidazolidinone 260.7 g, 1-methylcyclohexanol 80.5 g (purity 96%, 0.68 mol) and 95 wt % purity potassium hydroxide 20.5 g (0.35 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm². Next, while holding the gauge pressure at 1.8 kg/cm², the temperature was gradually increased. The reaction was carried out for about 9.4 hours after the reaction vessel internal temperature exceeded 130° C. During this time, the reaction was controlled so that the reaction vessel internal temperature did not exceed 145° C., then successively acetylene gas was refilled and the pressure inside the reaction vessel was held constantly at 1.8 kg/cm². After stopping the reaction, the residual acetylene gas was purged, the reaction solution was sampled, and gas chromatography was performed. As a result, the conversion of 1-methylcyclohexanol was 30.5%, while the selectivity of 1-methylcyclohexylvinyl ether was 29.4%. The volume of the absorbed acetylene (including amount dissolved in reaction solution) was 5.9 liters. This was 39% based upon the stoichiometric amount, and therefore, the percent of the acetylene which was effectively utilized for vinylization was 76%.

Part of the reaction solution which was obtained in Example 11 (38.9% based upon the total amount of reaction solution) was taken, the reaction solvent was washed off, then was distilled off under atmospheric pressure. The fraction distilled off at 165° C. in 3.0 g was collected. As a result of analysis by NMR, this was the 1-methylcyclohexylvinyl ether represented by the following formula (7).

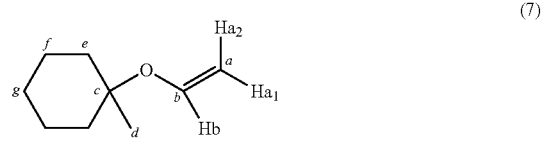

(7)

The results of NMR measurement of the resultant 1-methylcyclohexylvinyl ether are shown.

$^1$H-NMR (CDCl$_3$, TMS, 400 MHz): δ ppm 1.21 (s, 3H; d), 1.24-1.78 (m, 10H; e, f, g), 4.03 (dd, 1H, J=6.2, 0.3 Hz; Ha$_1$), 4.43 (dd, 1H, J=13.8, 0.4 Hz; Ha$_2$), 6.44 (dd, 1H, J=13.7, 6.2 Hz; Hb)

$^{13}$C-NMR (CDCl$_3$, 100 MHz): δ ppm 21.0 (f), 24.5 (g), 24.6 (d), 35.9 (e), 75.9 (c), 89.9 (a), 144.8 (b)

Example 12

A 2000 ml volume SUS autoclave equipped with a stirrer, pressure gauge, thermometer, gas introduction pipe and gas purge line was charged with 1,3-dimethyl-2-imidazolidinone 337.2 g, 1-methylcyclohexanol 13.8 g (purity 96%, 0.12 mol) and 95 wt % purity potassium hydroxide 3.6 g (0.06 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm$^2$. Next, while holding the gauge pressure at 1.8 kg/cm$^2$, the temperature was gradually increased. The reaction was carried out for about 0.9 hour after the reaction vessel internal temperature exceeded 130° C. During this time, the reaction was controlled so that the reaction vessel internal temperature did not exceed 145° C., then successively acetylene gas was refilled and the pressure inside the reaction vessel was held constantly at 1.8 kg/cm$^2$. After stopping the reaction, the residual acetylene gas was purged, the reaction solution was sampled, and gas chromatography was performed. As a result, the conversion of 1-methylcyclohexanol was 8.3%, while the selectivity of 1-methylcyclohexylvinyl ether was 8.3%. The volume of the absorbed acetylene (including amount dissolved in reaction solution) was 1.1 liters. This was 42% based upon the stoichiometric amount, and therefore, the percent of the acetylene which was effectively utilized for vinylization was 20%.

Example 13

A 2000 ml volume SUS autoclave equipped with a stirrer, pressure gauge, thermometer, gas introduction pipe and gas purge line was charged with 1,3-dimethyl-2-imidazolidinone 266.8 g, 2,5-dimethyl-2,5-hexanediol 160.2 g (purity 99%, 1.08 mol) and 95 wt % purity potassium hydroxide 29.3 g (0.50 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm$^2$. Next, while holding the gauge pressure at 1.8 kg/cm$^2$, the temperature was gradually increased. The reaction was carried out for about 11.7 hours after the reaction vessel internal temperature exceeded 150° C. During this time, the reaction was controlled so that the reaction vessel internal temperature did not exceed 161° C., then successively acetylene gas was refilled and the pressure inside the reaction vessel was held constantly at 1.8 kg/cm$^2$. After stopping the reaction, the residual acetylene gas was purged, the reaction solution was sampled, and gas chromatography was performed. As a result, the conversion rate of 2,5-dimethyl-2,5-hexanediol was 62.7%, the selectivity of 2,5-dimethyl-2,5-hexanediolmonovinyl ether was 38.9% and the selectivity of 2,5-dimethyl-2,5-hexanedioldivinyl ether was 4.2%. The volume of the absorbed acetylene (including amount dissolved in reaction solution) was 34.1 liters. This was 70% based upon the stoichiometric amount, and therefore, the percent of the acetylene which was effectively utilized for vinylization was 61%.

Example 14

A 2000 ml volume SUS autoclave equipped with a stirrer, pressure gauge, thermometer, gas introduction pipe and gas purge line was charged with 1,3-dimethyl-2-imidazolidinone 401.2 g, 2,5-dimethyl-2,5-hexanediol 45.0 g (purity 99%, 0.30 mol) and 95 wt % purity potassium hydroxide 8.1 g (0.14 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm$^2$. Next, while holding the gauge pressure at 1.8 kg/cm$^2$, the temperature was gradually increased. The reaction was carried out for about 1.7 hours after the reaction vessel internal temperature exceeded 150° C. During this time, the reaction was controlled so that the reaction vessel internal temperature did not exceed 161° C., then successively acetylene gas was refilled and the pressure inside the reaction vessel was held constantly at 1.8 kg/cm$^2$. After stopping the reaction, the residual acetylene gas was purged, the reaction solution was sampled, and gas chromatography was performed. As a result, the conversion of 2,5-dimethyl-2,5-hexanediol was 59.4%, the selectivity of 2,5-dimethyl-2,5-hexanediolmonovinyl ether was 14.8% and the selectivity of 2,5-dimethyl-2,5-hexanedioldivinyl ether was 2.7%. The volume of the absorbed acetylene (including amount dissolved in reaction solution) was 10.0 liters. This was 73% based upon the stoichiometric amount, and therefore, the percent of the acetylene which was effectively utilized for vinylization was 24%.

Comparative Example 1

A 2000 ml volume SUS autoclave equipped with a stirrer, pressure gauge, thermometer, gas introduction pipe and gas purge line was charged with N-methyl-2-pyrrolidone 266.6 g, 1-adamantanol 160.3 g (1.05 mol) and 95 wt % purity potassium hydroxide 6.38 g (0.11 mol). Nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm$^2$. Next, while holding the gauge pressure at 1.8 kg/cm$^2$, the temperature was gradually increased. The reaction was carried out for about 4.0 hours after the reaction vessel internal temperature exceeded 136° C. During this time, the reaction was controlled so that the reaction vessel internal temperature did not exceed 143° C., then successively acetylene gas was refilled and the pressure inside the reaction vessel was held constantly at 1.8 kg/cm$^2$. After stopping the reaction, the residual acetylene gas was purged, the reaction solution was sampled, and gas chromatography was performed. As a result, the conversion of 1-adamantanol was 1.3%, while the selectivity of 1-adamantylvinyl ether was 0.8%. The volume of the absorbed acetylene (including amount dissolved in reaction solution) was 2.3 liters. This was 10% based upon the stoichiometric amount, and therefore, the percent of the acetylene which was effectively utilized for vinylization was 8%.

Comparative Example 2

A 2000 ml volume SUS autoclave equipped with a stirrer, pressure gauge, thermometer, gas introduction pipe and gas purge line was charged with dimethylsulfoxide 267.8 g, 1-adamantanol 159.9 g (1.05 mol), and 95 wt % purity potassium hydroxide 6.35 g (0.11 mol), nitrogen gas was run, while stirring for about 60 minutes, and the inside of the vessel was replaced with nitrogen. Next, the reaction vessel was sealed and the inside of the vessel was charged with acetylene gas at a pressure of 1.8 kg/cm$^2$. Next, while holding the gauge pressure at 1.8 kg/cm$^2$, the temperature was gradually increased. The reaction was carried out for about 5 hours after the reaction vessel internal temperature exceeded 118° C. During this time, the reaction was controlled so that the reaction vessel internal temperature did not exceed 165° C., then successively acetylene gas was refilled and the pressure inside the reaction vessel was held constantly at 1.8 kg/cm². After stopping the reaction, the residual acetylene gas was purged, the reaction solution was sampled, and gas chromatography was performed. As a result, the conversion of 1-adamantanol was 11.3%, while the selectivity of 1-adamantylvinyl ether was 10.9%. The volume of the absorbed acetylene (including amount dissolved in reaction solution) was 13.8 liters. This was 59% based upon the stoichiometric amount, and therefore, the percent of the acetylene which was effectively utilized for vinylization was 18%.

The invention claimed is:

1. A method for producing vinyl ether represented by the formula (1):

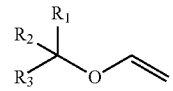
(1)

TABLE 1

| Solvent | | Concentration of total amount of alcohol and vinyl ether based upon the total amount including the other ingredients (wt %) | Alcohol | Base | Alcohol conversion (%) | Vinyl ether selectivity (%) | Absorbed acetylene (ratio to stoichiometric amount, %) | Acetylene consumed for vinylization (%) |
|---|---|---|---|---|---|---|---|---|
| Example 1 | 1,3-dimethyl-2-imidazolidinone | 36.9 to 39.8 | 1-adamantanol | Potassium hydroxide | 97.9 | 97.3 | 120 | 81 |
| Example 2 | 1,3-dimethyl-2-imidazolidinone | 36.4 to 39.0 | 1-adamantanol | Potassium t-butoxy | 98.1 | 96.8 | 123 | 79 |
| Example 3 | 1,3-dimethyl-2-imidazolidinone | 36.5 to 38.4 | 1-adamantanol | Potassium t-butoxy | 99.9 | 97.1 | 135 | 72 |
| Example 4 | 1,3-dimethyl-2-imidazolidinone | 36.6 to 38.2 | 1-adamantanol | Potassium t-butoxy | 99.8 | 98.3 | 168 | 59 |
| Example 5 | 1,3-dimethyl-2-imidazolidinone | 17.7 to 18.6 | 1-adamantanol | Potassium hydroxide | 56.8 | 55.9 | 119 | 47 |
| Example 6*[1] | 1,3-dimethyl-2-imidazolidinone | 38.5 to 42.5 | 1-adamantanol | Potassium hydroxide | 97.2 | 97.1 | — | — |
| Example 7 | 1,3-dimethyl tetrahydropyrimidi-2-one | 37.2 to 38.5 | 1-adamantanol | Potassium hydroxide | 50 | 49.7 | 75 | 66 |
| Example 8 | Triethylene glycol dimethyl ether | 36.3 to 38.5 | 1-adamantanol | Potassium hydroxide | 77.5 | 77.1 | 103 | 75 |
| Example 9 | Tetraethylene glycol dimethyl ether | 37.1 to 37.8 | 1-adamantanol | Potassium hydroxide | 37.4 | 36.8 | 57 | 65 |
| Example 10 | 1,3-dimethyl-2-imidazolidinone | 5.9 to 6.1 | 1-adamantanol | Potassium hydroxide | 27.8 | 27.1 | 98 | 28 |
| Example 11 | 1,3-dimethyl-2-imidazolidinone | 22.3 to 22.2 | 1-methylcyclohexanol | Potassium hydroxide | 30.5 | 29.4 | 39 | 76 |
| Example 12 | 1,3-dimethyl-2-imidazolidinone | 3.9 to 3.8 | 1-methylcyclohexanol | Potassium hydroxide | 8.3 | 8.3 | 42 | 20 |
| Example 13 | 1,3-dimethyl-2-imidazolidinone | 35.1 to 28.4 | 2,5-dimethyl-2,5-hexanediol | Potassium hydroxide | 62.7 | 43.1*[2] | 70 | 61 |
| Example 14 | 1,3-dimethyl-2-imidazolidinone | 9.9 to 5.9 | 2,5-dimethyl-2,5-hexanediol | Potassium hydroxide | 59.4 | 17.5*[2] | 73 | 24 |
| Comp. Ex. 1 | N-methyl-2-pyrrolidone | 37.0 to 36.7 | 1-adamantanol | Potassium hydroxide | 1.3 | 0.8 | 10 | 8 |
| Comp. Ex. 2 | Dimethyl sulfoxide | 36.8 to 36.0 | 1-adamantanol | Potassium hydroxide | 11.3 | 10.9 | 59 | 18 |

*[1]Acetylene run under atmospheric pressure. Other examples and comparative examples performed using sealed vessel and reaction at 0.18 kg/cm² (gauge pressure).
*[2]Value calculated as total of monovinyl ether and divinyl ether As is clear from the results of Comparative Example 2 of Table 1, in the conventional reaction of alcohol and acetylene, when using the dimethyl sulfoxide described representatively in many publications, sufficient conversion of alcohol is not obtained for the amount of acetylene which is consumed, and therefore, this is not efficient. Further, from the results of Comparative Example 1, when using N-methyl-2-pyrrolidone, similarly the alcohol conversion is insufficient and, further, significant absorption of acetylene under a low acetylene pressure is not exhibited.

On the other hand, in Examples 1 to 14 using the production method of vinyl ether according to the present invention, it is possible to vinylize the low reactivity tertiary alcohol under a low acetylene pressure fast and efficiently and possible to obtain high purity vinyl ether.

from acetylene and a tertiary alcohol in the presence of a base, characterized in that;

the tertiary alcohol is an alcohol represented by the formula (2):

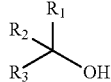
(2)

and that a reaction is carried out by using, as a solvent, a cyclic urea compound represented by the formula (3):

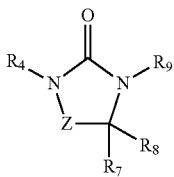

(3)

wherein Z indicates

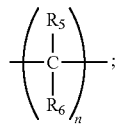

wherein, in the above formulae (1) to (3),
$R_1$ to $R_3$ independently indicate $C_1$ or more hydrocarbon groups represented by the following formula (5)

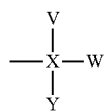

(5)

wherein
X is a carbon atom,
V and W independently indicate hydrogen or a substituted or unsubstituted $C_1$ or more hydrocarbon group, provided that the case where the carbon directly bonded with X of V or W has a primary or secondary hydroxyl group in a cis arrangement with a hydroxyl group of the tertiary alcohol (2), as a substituent group is excluded, and
Y indicates hydrogen or a substituted or unsubstituted $C_1$ or more hydrocarbon group, provided that the case where the carbon of Y directly bonded with X has a primary or secondary hydroxyl group in a cis arrangement with a hydroxyl group of the tertiary alcohol (2) as a substituent group is excluded; or one group selected form a tertiary hydroxyl group, alkoxy group and alkyl sulfanyl group,
two or more of $R_1$ to $R_3$ may be condensed to form a ring, provided that the case where two or more of $R_1$ to $R_3$ are condensed to form an aromatic ring is excluded,
further, $R_4$ to $R_9$ independently indicate hydrogen or a $C_1$ or more alkyl group or —$(CH_2CH_2O)_mR_{10}$,
$R_{10}$ indicates hydrogen or a $C_1$ to $C_4$ saturated or unsaturated hydrocarbon group,
m is an integer of 1 or more, and n is an integer of 1 to 4.

2. A method for producing vinyl ether as claimed in claim 1, wherein said tertiary alcohol is at least one member selected from the group consisting of 2,5-dimethyl-2,5-hexanediol, 1-methylcyclohexanol, 1-adamantanol and adamantane-1,3-diol.

3. A method for producing vinyl ether as claimed in claim 1, wherein a total concentration of the alcohol and the resultant vinyl ether in the reaction system is 17% by weight or more.

4. A method for producing vinyl ether as claimed in claim 1, wherein a total concentration of the tertiary alcohol and the resultant vinyl ether in the reaction system is 25 to 90% by weight.

5. A method for producing vinyl ether as claimed in claim 1, wherein, as the cyclic urea compound, a cyclic urea compound wherein, in the formula (3), $R_4$ and $R_9$ are independently alkyl groups and $R_5$, $R_6$, $R_7$ and $R_8$ are independently hydrogen or an alkyl group is used.

6. A production method as claimed claim 1, wherein the cyclic urea compound is 1,3-dimethyl-2-imidazolidinone or 1,3-dimethyltetrahydropyrimidin-2-one or a mixture thereof.

7. A method for producing vinyl ether as claimed in claim 1, wherein the base is at least one base selected from the group consisting of potassium hydroxide, sodium hydroxide and potassium t-butoxy.

8. A method for producing vinyl ether as claimed in claim 1, wherein a pressure of the acetylene is 2 kg/cm$^2$ (gauge pressure) or less.

9. A method for producing vinyl either as claimed in claim 1, wherein the pressure of the acetylene is atmospheric pressure to 1.8 kg/cm$^2$ (gauge pressure) or less.

* * * * *